(12) United States Patent
Gordon et al.

(10) Patent No.: US 10,080,662 B2
(45) Date of Patent: Sep. 25, 2018

(54) PATIENT-SPECIFIC CRANIOFACIAL IMPLANTS

(71) Applicants: Howmedica Osteonics Corp., Mahwah, NJ (US); Chad Gordon, Lutherville, MD (US)

(72) Inventors: Chad Gordon, Lutherville, MD (US); John Rocco Bryndza, Westwood, NJ (US); Tahir Bisic, New York, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 14/958,161

(22) Filed: Dec. 3, 2015

(65) Prior Publication Data
US 2016/0081805 A1    Mar. 24, 2016

Related U.S. Application Data

(62) Division of application No. 13/963,225, filed on Aug. 9, 2013, now Pat. No. 9,216,084.

(51) Int. Cl.
*A61F 2/28* (2006.01)
*A61F 2/00* (2006.01)
*A61F 2/30* (2006.01)

(52) U.S. Cl.
CPC .......... *A61F 2/2875* (2013.01); *A61F 2/0059* (2013.01); *A61F 2/28* (2013.01);
(Continued)

(58) Field of Classification Search
CPC ... A61F 2/28; A61F 2/2875; A61F 2002/2882
(Continued)

(56) References Cited

U.S. PATENT DOCUMENTS

| 4,436,684 A | 3/1984 | White |
| 4,990,160 A * | 2/1991 | Terino ................... A61F 2/2803 623/17.18 |

(Continued)

FOREIGN PATENT DOCUMENTS

| EP | 1957128 A2 | 8/2008 |
| JP | 2001092950 A | 4/2001 |
| RU | 2074672 C1 | 3/1997 |

OTHER PUBLICATIONS

Synthes CMF Customized Surgical Solutions—PSI Ordering Process, ® 2006-2012.
(Continued)

*Primary Examiner* — Dinah Baria
(74) *Attorney, Agent, or Firm* — Lerner, David, Littenberg, Krumholz & Mentlik, LLP (57) ABSTRACT

Disclosed herein are patient-specific craniofacial implants structured for filling bone voids in the cranium as well as for simultaneously providing soft tissue reconstruction and/or augmentation for improved aesthetic symmetry and appearance. Pterional voids or defects generally result from a chromic skull deformity along with a compromised temporalis muscle or soft tissue distortion from previous surgery. When muscle atrophy occurs in the pterion, temporal hollowing generally results where there would be soft tissue but for the atrophy. The patient-specific temporal implants herein are configured to have an augmented region adjacent the temporal region of the cranium in order to account for and correct any such temporal hollowing.

16 Claims, 8 Drawing Sheets

(52) U.S. Cl.
CPC . *A61F 2/30942* (2013.01); *A61F 2002/30948* (2013.01); *A61F 2002/30952* (2013.01); *A61F 2240/002* (2013.01)

(58) Field of Classification Search
USPC .......................................... 623/17.18, 17.19
See application file for complete search history.

(56) References Cited

U.S. PATENT DOCUMENTS

| | | | |
|---|---|---|---|
| 5,195,951 | A | 3/1993 | Giampapa |
| 5,380,329 | A | 1/1995 | Elia et al. |
| 5,391,181 | A | 2/1995 | Johnson et al. |
| 5,421,831 | A | 6/1995 | Giampapa |
| 5,514,179 | A | 5/1996 | Brennan |
| 5,658,516 | A | 8/1997 | Eppley et al. |
| RE37,249 | E | 6/2001 | Leibinger et al. |
| 6,254,639 | B1 | 7/2001 | Peckitt |
| 6,277,150 | B1 | 8/2001 | Crawley et al. |
| 6,302,884 | B1 | 10/2001 | Wellisz et al. |
| 6,551,608 | B2 | 4/2003 | Yao |
| 6,582,435 | B2 | 6/2003 | Wellisz et al. |
| 7,747,305 | B2 | 6/2010 | Dean et al. |
| 8,298,292 | B2 | 10/2012 | Swords et al. |
| 8,781,557 | B2 | 7/2014 | Dean et al. |
| 9,208,558 | B2 | 12/2015 | Dean et al. |
| 9,275,191 | B2 | 3/2016 | Dean et al. |
| 9,292,920 | B2 | 3/2016 | Dean et al. |
| 9,330,206 | B2 | 5/2016 | Dean et al. |
| 2004/0138591 | A1 | 7/2004 | Iseki et al. |
| 2006/0094951 | A1* | 5/2006 | Dean ................... A61F 2/30942 600/407 |
| 2006/0116682 | A1 | 6/2006 | Longo |
| 2006/0217813 | A1 | 9/2006 | Posnick et al. |
| 2007/0067041 | A1 | 3/2007 | Kotoske |
| 2012/0010711 | A1 | 1/2012 | Antonyshyn et al. |
| 2012/0203289 | A1 | 8/2012 | Beerens et al. |
| 2012/0259428 | A1 | 10/2012 | Brogan et al. |
| 2012/0265312 | A1 | 10/2012 | Burke et al. |
| 2012/0330427 | A1 | 12/2012 | Yaremchuk |
| 2012/0330435 | A1 | 12/2012 | Engqvist et al. |
| 2013/0206626 | A1 | 8/2013 | Schindel et al. |
| 2013/0289727 | A1* | 10/2013 | Rudnick ............... A61F 2/2875 623/17.19 |

OTHER PUBLICATIONS

HTR®-PMI CT-Scanning Protocol, Biomet HTR-PMI Brochure (date unknown).
Kelyniam Request for Quote form, undated.
KLS martin Group, Patient Contoured Mesh Order and Upload Form <http://pcm.klsmartinusa.com>, undated.
KLS martin Group, Patient Contoured Mesh Instructions <http://pcm.klsmartinusa.com/instructions.html>, undated.
OsteoMatch Patient Matched Implants, OsteoMed Neurosurgical, undated.
Osteosymbionics Clearshield Craniofacial Implant, undated.
Osteosymbionics, Custom Craniofacial Prosthesis CT Scanning Protocol, undated.
Osteosymbionics, ST Temporalis Soft Tissue Implant, undated.
Synthes CMF,CT Scanning Protocol Synthes Patient Specific Implants, Copyright 2007.
Synthes CMF, PSI-Patient Specific Implants, Derived from CT data excellent reconstructive results, Copyright 2004.
Stryker CMF Customized Implant PMMA, Surgical Protocol, Copyright 2013 Stryker.
Stryker CMF Customized Implant MEDPOR, Surgical Protocol, Copyright 2012 Stryker.
Stryker CMF Customized Implant PEEK, Surgical Protocol, Copyright 2013 Stryker.
Windhager, et al., "Limb Salvage in Periacetabular Sarcomas: Review of 21 Consecutive Cases", Reprinted from Clinical Orthopedics, Oct. 1996, vol. 331, pp. 265-276.
MEK Medizinelektronik GmbH, "Three Dimensions. Nothing Less. Organ Models for Surgery Planning", Endoplan, Copyright 1988.
MEK Medizinelektronik GmbH, "Innovations made in Germany", Copyright Oct. 1988.
Howmedica, "Howmedica Computer Tomography Evaluation System (HCTE)", date unknown.

* cited by examiner

PATIENT-SPECIFIC CRANIOFACIAL IMPLANTS

CROSS-REFERENCE TO RELATED APPLICATION

The present application is a divisional of the U.S. patent application Ser. No. 13/963,225, filed on Aug. 9, 2013, the disclosure of which is incorporated herein by reference.

FIELD OF THE INVENTION

The present invention relates to patient-specific craniofacial implants and methods of designing such implants for filling both bone and soft tissue in the temporal region of a patient's head.

BACKGROUND OF THE INVENTION

Certain congenital conditions and acquired deformities related to surgery, irradiation, and/or trauma may result in varying sized and shaped voids in bone and soft tissue. For example, severe impacts to the head could leave the frontal, parietal and/or temporal areas of the craniofacial skeleton in need of repair. Cranial bone voids are commonly filled throughout the anterior, middle, and posterior cranial vaults, for example, using autologous bone flaps, standard or customized alloplastic implants, titanium mesh, biologic absorbable materials, tissue engineered substrates and/or liquid methyl methacrylate in order to provide much needed cerebral protection. However, in times where secondary cranioplasty requires a bone substitute, temporal hollowing needs to be corrected and/or prevented.

While cranial bone voids present via congenital deformities or traumatic injuries may be filled using any one or more of the above means to achieve structural soundness, replacement of soft tissue structures that overlie the bone void being filled and underlie adjacent skin tissue generally has to be accounted for in order to achieve a preferable cosmetic result. Bone flaps, standard or customized alloplastic implants, titanium mesh, and liquid methyl methacrylate that are used to fill bone voids do not account for soft tissue atrophy in the temporal area of the skull. Thus, these bone void filling means do not provide an adequate aesthetic reconstruction of this area.

In many cases where bone is filled in the temporal region, the soft tissue loss in this area generally results in concavity referred to as temporal hollowing. This reflects a deficiency in the bulk of the temporalis muscle or overlying temporal fat pad. Many patients who have undergone neurosurgical procedures that damage the integrity of the temporalis muscle during temporal or pterional craniotomy surgery in the temporal area are left with this concavity. Both aesthetic and reconstructive procedures that violate the temporal fat pad may result in temporal hollowing. As such, the area of concern is a direct deformity related to a few etiologies such as temporalis muscle displacement or foreshortening from previous surgery, temporal fat pad atrophy, or soft tissue contraction from irradiation or aging.

In patients with the common temporal hollowing, the top or cephalad part of the deformity is generally a concave depression due to the missing, above-mentioned etiologies. In addition, directly underneath and neighboring this concave depression is a convex bulge (directly cephalad to the zygomatic arch) that often originates from a displaced temporalis muscle. In some common instances, the temporalis muscle cannot be re-inserted since the bone flap is unable to be placed back into position, thereby leaving an absent fixation point adjacent the temporal crest. This not only accentuates the neighboring concave deformity above, it sometimes causes dynamic distortion during chewing since the temporalis muscle is involved with mastication.

Other reasons for the cephalad deficiency, or other head deformities, may entail temporal fat pad wasting, which is a defined layer of anatomical fat between the skin and the skull which adds to the normal bulk of one's temporal region. It is often a sign of youthfulness. Many patients who have undergone neurosurgical and/or temporal procedures may lose the integrity of the temporalis muscle during temporal or pterional craniotomy surgery. Both aesthetic and reconstructive procedures that violate the temporal fat pad, such as coronal incisional approaches, for instance, may also result in temporal hollowing, which can happen if a surgeon devascularizes the area with dissection or if the area has received irradiation or tissue resection for oncological treatment.

Numerous techniques have been described to augment the temporal area, including the placement of various standard or customized alloplastic implants, titanium mesh, free fat grafts, dermal grafts, tissue engineered substrates, the injection and onlay of various absorbable and permanent materials, loco-regional flaps, and, in some instances, free tissue transfer with microscopic technique. Temporal augmentation can restore the preoperative appearance of these patients; however, such augmentation is generally performed in a subsequent procedure after an initial procedure of filling a bone void in this area. Thus, these solutions are problematic because a revision surgery is generally required to correct the deformity, and the patient will likely exhibit aesthetic asymmetry prior to the revision surgery. There thus exists a need for a patient-specific cranial implant that provides both bony reconstruction and soft tissue reconstruction such that one or more revision surgeries will generally not be necessary.

BRIEF SUMMARY OF THE INVENTION

As used herein, when referring to bones or other parts of the body, the term "superior" or "cephalad" means upper or top, and the term "inferior" or "caudal" means lower or bottom. The term "posterior" means towards the back of the body, and the term "anterior" means towards the front part of the body or the face. The term "medial" means toward the midline or center of the body, and the term "lateral" means away from the midline or outside of the body.

The patient-specific, dual-purpose temporal implants of the present invention are designed to fill a void in the skull while also simultaneously augmenting the pterional/temporal area. Preferably, alloplastic material is used in the construction of such patient-specific temporal implants. The mechanical properties of the alloplastic material used to construct these implants will allow them to cover the void and to recreate the soft tissue bulk that is preferably present in the temporal area prior to any injury and/or atrophy occurring in a patient. The patient-specific implants of the present invention are designed to fill a cranial void while also restoring aesthetic symmetry by augmenting the temporal area of the skull to counter temporal hollowing. Therefore, the patient-specific cranial implants of the present invention may be used to replace a bony void left by a craniotomy either as a preemptive or prophylactic solution to addressing aesthetic asymmetry that may occur due to atrophy of temporal muscle or overlying fat pad of the bony void.

A first aspect of the present invention is a method of designing a patient-specific craniofacial implant for filling a void in a patient's skull and for simultaneously replacing soft tissue comprises first creating a three dimensional model of the skull having the void, then creating a preliminary implant model configured to replace the void in the skull, and then creating an updated implant model by augmenting an outer contour of the preliminary implant model to account for soft tissue loss or displacement in a temporal area such as the pterional region of the skull overlying at least a portion of the bony void.

In one embodiment of this first aspect, tomographic images of the skull of the patient are taken in order to create the three dimensional model of the skull including the void. The preliminary model is created by mirroring contralateral bone of the void about a sagittal plane of the patient. If the defect is bilateral, normal variations of soft tissue to hard tissue variance may be assessed by industry standards and utilized for unilateral or bilateral temporal implant fabrication. Such assessments may be made as gender-specific for males and females since they are known to have different gender-specific anthropometrics.

In another embodiment of this first aspect, creating a three dimensional of the skull having the void may include taking two-dimensional or three-dimensional photographs from various views for confirmation of aesthetic deformity size and/or shape of the void.

In another embodiment of this first aspect, augmenting the outer contour of the preliminary implant model comprises providing a first cross-sectional view of the preliminary implant model in a coronal plane, providing on the first cross-sectional view a vertical line tangent to a most lateral portion of a zygomatic arch of the skull of the patient, and providing on the first cross-sectional view a contour line from a temporal crest of the skull until the contour line intersects the vertical line tangent to the most lateral portion of the zygomatic arch in the first cross-sectional view, the contour line representing a first portion of the augmented outer contour of the preliminary implant model.

In yet another embodiment of this first aspect, augmenting the outer contour of the preliminary implant model further comprises providing a second cross-sectional view of the preliminary implant model in a coronal plane, providing on the second cross-sectional view a vertical line tangent to a most lateral portion of a zygomatic arch of the skull of the patient, and providing on the second cross-sectional view a contour line from a temporal crest of the skull until the contour line intersects the vertical line tangent to the most lateral portion of the zygomatic arch in the second cross-sectional view, the contour line representing a second portion of the augmented outer contour of the preliminary implant model. The coronal plane of the first cross-sectional view is more posterior than the coronal plane of the second cross-sectional view.

In still yet another embodiment of this first aspect, augmenting the outer contour of the preliminary implant occurs in a plurality of cross-sectional views in the coronal plane.

In still yet another embodiment of this first aspect, augmenting the outer contour of the preliminary implant occurs in a plurality of cross-sectional views in an axial plane.

In still yet another embodiment of this first aspect, augmenting the outer contour of the preliminary implant occurs in a plurality of cross-sectional views in a sagittal plane.

In still yet another embodiment of this first aspect, the patient-specific craniofacial implant is manufactured from alloplastic and/or absorbable biologic materials selected from one member of a group consisting of polymethylmethacrylate (PMMA), polyetheretherketone (PEEK), and porous high-density polyethylene (MedPor). Other biologic materials or tissue-engineered substrates may be used in both allograft and xenograft origin using the patient-specific craniofacial implant design processes described herein.

A second aspect of the present invention is a craniofacial implant comprising a base portion having an outer surface curved in a medial to lateral direction, a superior to inferior direction, and a posterior to anterior direction, and a curved augment portion protruding outwardly from the outer surface of the base portion in the medial to lateral direction to restore proper appearance anywhere along the temporal skeleton when both a hard tissue deformity and soft tissue deformity co-exist. The craniofacial implant of the present invention could also be designed for soft-tissue only defects, providing the surgeon a new method to camouflage assymetries—both from congential and acquired etiologies.

In one embodiment of this second aspect, the curved augment portion of the craniofacial implant has an outer surface curved in the medial to lateral direction, the superior to inferior direction, and the posterior to anterior direction.

In another embodiment of this second aspect, the outer surface of the base portion and the augment portion has a first radius of curvature in the medial to lateral direction, and wherein the first radius of curvature of the base portion is larger than the first radius of curvature of the augment portion.

In yet another embodiment of this second aspect, the outer surface of the base portion and the augment portion has a second radius of curvature in the superior to inferior direction, and wherein the second radius of curvature of the base portion is larger than the second radius of curvature of the augment portion.

In yet another embodiment of this second aspect, the outer surface of the base portion and the augment portion has a third radius of curvature in the posterior to anterior direction, and wherein the third radius of curvature of the base portion is larger than the third radius of curvature of the augment portion.

In yet another embodiment of this second aspect, the outer surfaces of the base portion and the augment portion are convex.

In still yet another embodiment of this second aspect, the base portion and the augment portion each have concave inner surfaces.

In still yet another embodiment of this second aspect, the base portion has a lateral side that forms a perimeter of the craniofacial implant.

In still yet another embodiment of this second aspect, the augment portion has a lateral side that forms a portion of a perimeter of the base portion.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Figure 1A:
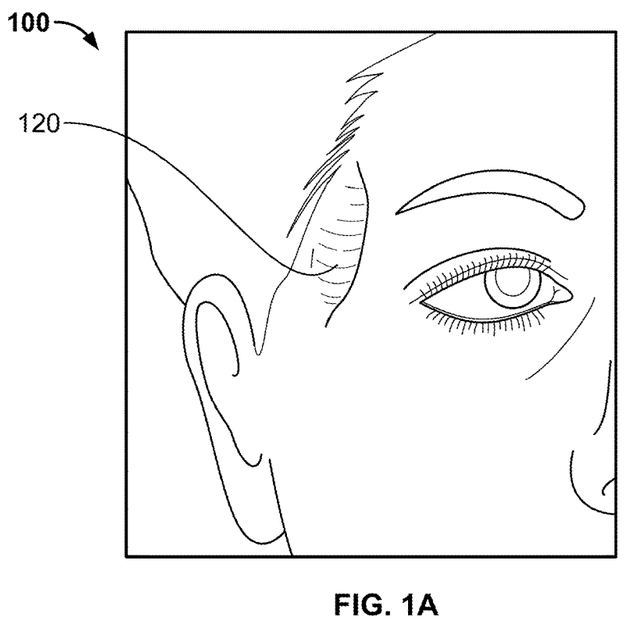
FIG. 1A is a perspective view of a patient's face exhibiting temporal hollowing in the pterional region of the skull.

FIG. 1A is a perspective view of a patient's face 100 exhibiting temporal hollowing 120 in the pterional region of the skull of the patient. The size, shape and location of such temporal hollowing of a patient may differ based on patient's anatomy as well as the type of injury and/or the amount of tissue atrophy incurred by the patient in this region.

Figure 1B:
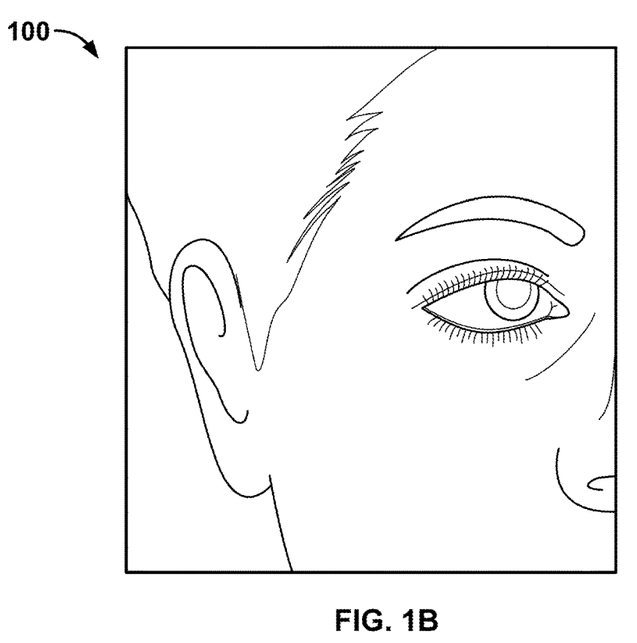
FIG. 1B is a perspective view of the patient's face of FIG. 1A with a repaired pterional region such that the temporal hollowing has been corrected.

FIG. 1B is a perspective view of the patient's face with a repaired pterional region such that the temporal hollowing has been corrected and is no longer present. After an initial surgery to correct a bony void is performed, a subsequent procedure using a pterional graft, PMMA, filler, absorbable material or tissue engineered substrate, for example, may be performed in order to repair the soft tissue defect. The subsequent procedure may be conducted via injection of PMMA percutaneously into this region or by placing a pterional flap through a small incision made in the skin. However, a patient will likely exhibit aesthetic asymmetry between the time of the initial surgery and the subsequent revision surgery to correct the temporal hollowing shown in FIG. 1A. The patient-specific cranial implants and methods of designing such implants of the present invention together provide simultaneous customized hard tissue (i.e. bony) reconstruction and soft tissue (i.e. fat/muscle) reconstruction in a single procedure approach such that temporal hollowing is avoided and revision procedures will not be required.

Figure 2:
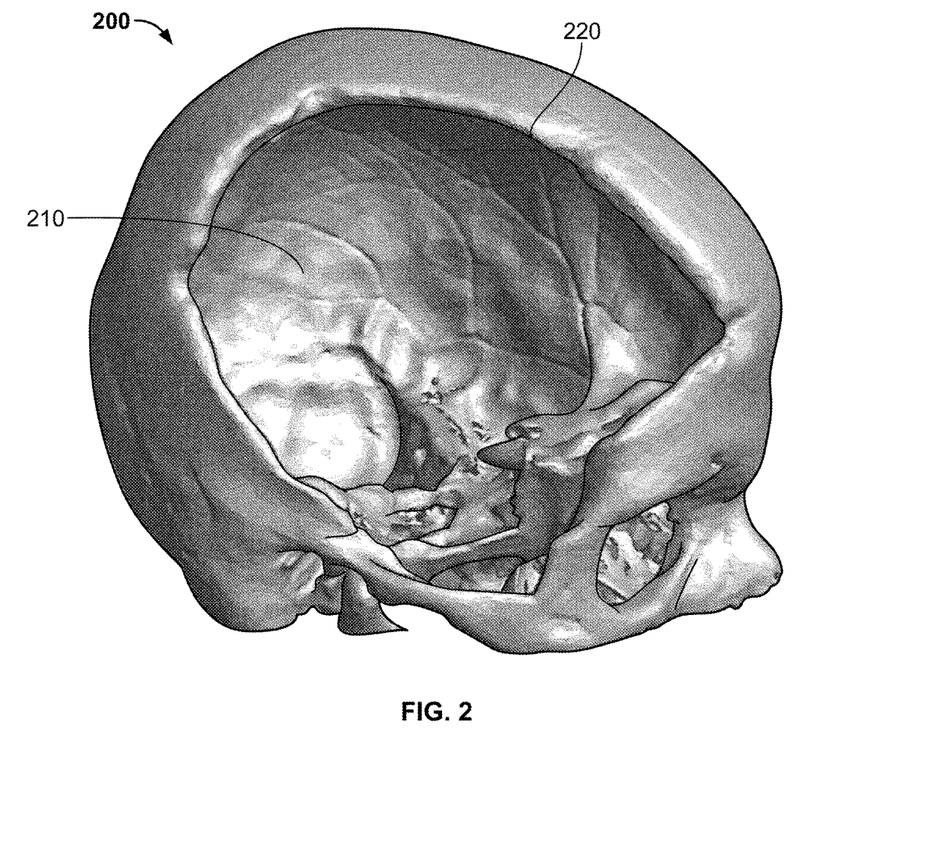
FIG. 2 is a perspective view of a patient's skull exhibiting a large bone void predominately positioned in the temporal lobe thereof.
Figures 3A, 3B:
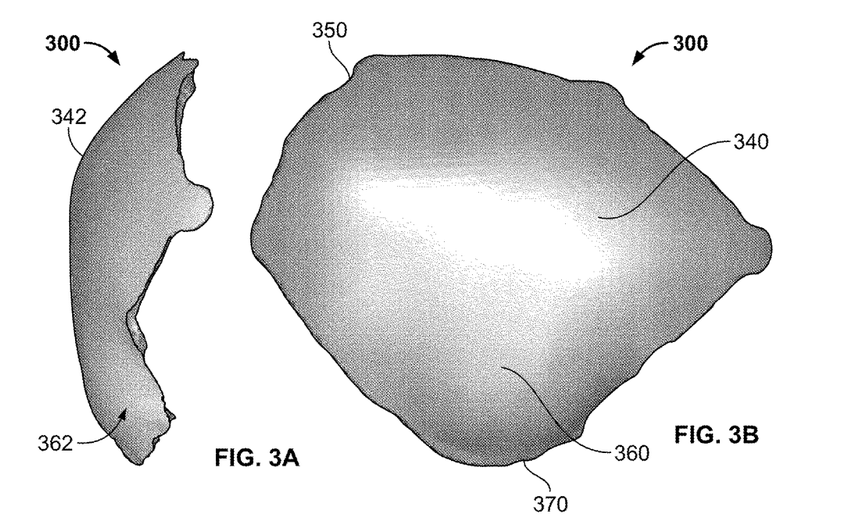
FIG. 3A is a frontal view of one embodiment of a patient-specific cranial implant of the present invention designed to fill a bone void in a skull of a patient.
FIG. 3B is a lateral view of an outer surface of the patient-specific cranial implant of FIG. A.
Figure 3C:
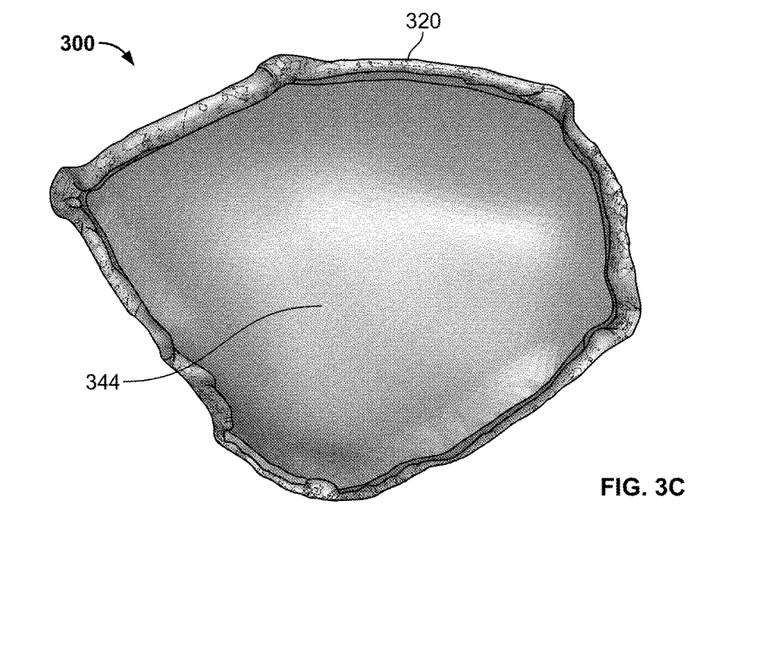
FIG. 3C is a lateral view of an inner surface of the patient-specific cranial implant of FIG. 3A.

FIG. 2 is a perspective view of a patient's skull 200 exhibiting a large irregularly shaped bone void 210 predominately positioned in the temporal lobe thereof. FIGS. 3A-3C show one embodiment of a patient-specific cranial implant 300 of the present invention designed to fill a bone void, such as shown in FIG. 2, for example. Patient-specific cranial implant 300 includes a perimeter 320 configured to contact a perimeter 220 of bone void 210 when patient-specific cranial implant 300 is coupled to bone void 210 in a preoperatively planned position. Upon coupling of patient-specific cranial implant 300 to bone void 210, plates, fasteners and/or adhesive glue, for example, may be used around perimeters 220, 320 of bone void 210 and implant 300, respectively, in order to fix the position of implant 300 with respect to bone void 210. A description of such plates and fasteners used to couple a patient-specific implant to a perimeter of a bone void is shown and described in the surgical protocol titled "Stryker CMF Customized Implant PEEK," the disclosure of which is incorporated by reference herein in its entirety.

Implant 300 includes a base portion 340 and an augment portion 360. Base portion 340 includes a convex outer surface 342 and a concave inner surface 344. Outer and inner surfaces 342, 344 of base portion 340 are preferably curved in a superior to inferior direction, a posterior to anterior direction, and a medial to lateral direction. Augment portion 360 protrudes outwardly from base portion 340 in the medial to lateral direction. Augment portion 360 includes a convex outer surface 362 that is also preferably curved in the superior to inferior direction, the posterior to anterior direction, and the medial to lateral direction.

Base portion 340 and augment portion 360 each have a first radius of curvature in the superior to inferior direction, a second radius of curvature in the posterior to anterior direction and a third radius of curvature in the medial to lateral direction. The first, second and third radii of curvature of the base portion 340 are all larger than the first, second and third radii of curvature of the augment portion 360, respectively. Therefore, base portion 340 is flatter and not as steeply shaped as augment portion 360. The radii of curvature are generally not constant along any one direction for each of the base portion 340 and augment portion 360.

Augment portion 360 has a lateral side 370 that preferably forms a portion of a perimeter 350 of base portion 340. The location of augment portion 360 with respect to base portion 360 is such that lateral side 370 of augment portion 360 preferably forms a portion of perimeter 320 of implant 300 along with perimeter 350 of base portion 340.

When cranial implant 300 is implanted, the most lateral portion of outer surface 362 of augment portion 360 is preferably located on a line tangent to the most lateral portion of the zygomatic arch, the line being substantially parallel to the sagittal plane of the patient. Augment portion 360 also extends as far posteriorly as it does superiorly so that an area of augment portion is roughly square.

A method of designing a patient-specific craniofacial implant, such as cranial implant 300, for filling a void in a skull of a patient and for replacing soft tissue is shown in FIGS. 4A-6B. A tomographic scan such as a computed tomography ("CT") scan of a patient with a lateral cranial defect that fully or partially extends into the pterional region of the skull is first taken. Off the shelf CT segmentation software is then used to create a three dimensional ("3D") model of the patient's cranium including the lateral cranial defect. A patient-specific craniofacial implant is then designed using computer aided design ("CAD") software. The patient-specific 3D implant will fill the bony void left by a craniotomy, for example, and also augment the visible temporal portions of the patient's head.

Figure 4A:
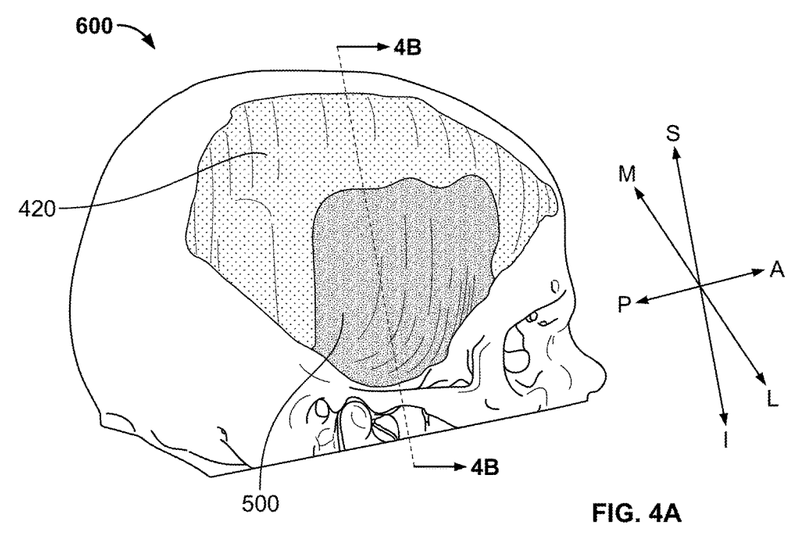
FIG. 4A is a 3D reconstruction of a patient-specific cranial implant of the present invention having filled a void in the skull of a patient, the patient-specific cranial implant having an augmented portion projecting outwardly from a base portion.
Figure 4B:
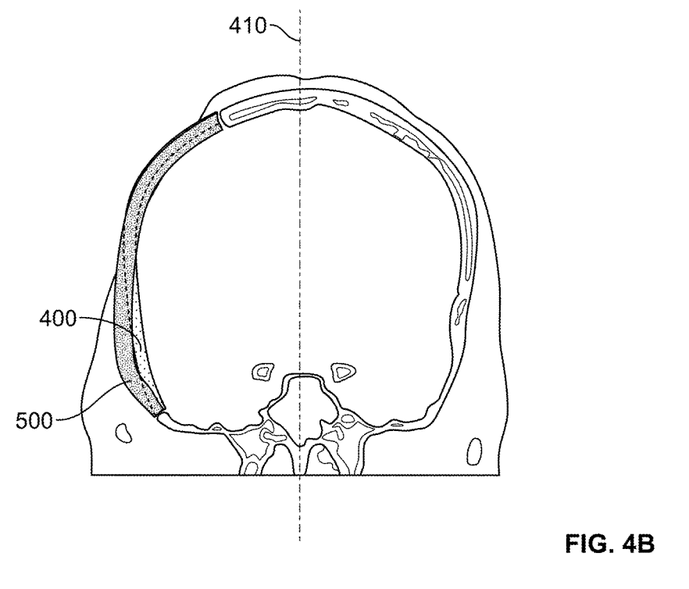
FIG. 4B is a coronal cross-section of the 3D reconstruction of FIG. 4A taken along the section line shown in FIG. 4A, the cross-section showing the relationship between the base portion and the augmented portion of the patient-specific cranial implant.

Using the CAD software, a preliminary implant model 400 is designed by mirroring contralateral bone of the lateral cranial defect. Generally, the contralateral bone is mirrored off of the central sagittal plane 410 as shown in FIG. 4B of a patient's skull in order to define the size, shape and location of preliminary implant model 400 with respect to the cranial defect. Models of deformed or missing segments of internal structures, such as a lateral cranial defect, may also be constructed from coordinate data specifying the deformed or missing segment that is derived from representations of a normal mirror image segment of the structure. For example, coordinate data defining a mirror image segment of a structure is useful in the construction of an implantable prosthetic inlay that is to replace a missing segment of a generally symmetrical internal anatomic structure as shown and described in U.S. Pat. No. 4,436,684 to White entitled, "Method of Forming Implantable Prosthesis for Reconstructive Surgery," the disclosure of which is hereby incorporated by reference in its entirety. In instances where bilateral deformities exist, the dual-purpose implants of the present invention may be at least partly designed using standard gender-specific dimensions.

While preliminary implant model 400 may be designed using any one or more of the above described methods, it represents a traditional customized implant that does not account for soft tissue in the pterional/temporal region. In a method of the present invention, preliminary implant model 400 is used as a guide during subsequent design steps. The outer contour 420 of preliminary implant model 400 is augmented in order to account for the soft tissue loss.

Preliminary implant model 400 is designed to have a perimeter that contacts the entire perimeter of the bone void. Augment portion 500 is designed to augment the pterion in order to counter the effects of temporal hollowing. Careful attention is made not to include excess material inferiorly which may contribute to mandibular interference known as trismus. The CT coronal cross section of FIG. 4B shows the difference between preliminary implant model 400 and an updated implant model including augment portion 500. In some design processes, augment portion 500 may only project outwardly from preliminary implant model 400 such that it does not span the entire length of a bone void, and therefore does not contact the entire perimeter of the bone void as does the preliminary implant model. As can be seen in FIG. 4B, for example, augment portion 500 is not symmetric to contralateral bone as is preliminary implant model 400. Together, preliminary implant model 400 and augment portion 500 form an updated implant model 600 as shown in FIG. 4A. Preliminary implant model 400 has a first volume and augment portion 500 has an additional volume. With the addition of the volume of augment portion 500 to the first volume of preliminary implant model 400, updated implant model 600 therefore has a second volume greater than the first volume. This figure also includes a directional legend with arrows in three dimensions. S, I, M, L, P and A on this legend, and any other legend in the drawings, stand for superior, inferior, medial, lateral, posterior and anterior, respectively. Most of the bulk reproduction of the soft tissue in the pterion region, which is represented by augment portion 500, occurs at the anterior, lateral, inferior portion of the temporal skull.

Figure 5A:
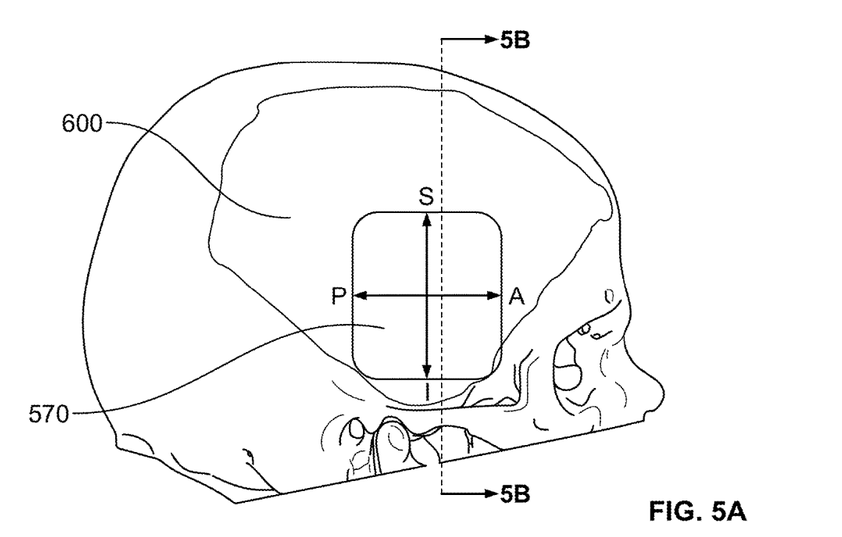
FIG. 5A is a 3D reconstruction of the patient-specific cranial implant of FIG. 4A wherein the augmented portion thereof is shown having an area approximately the area of the box with arrows overlying the implant.
Figure 5B:
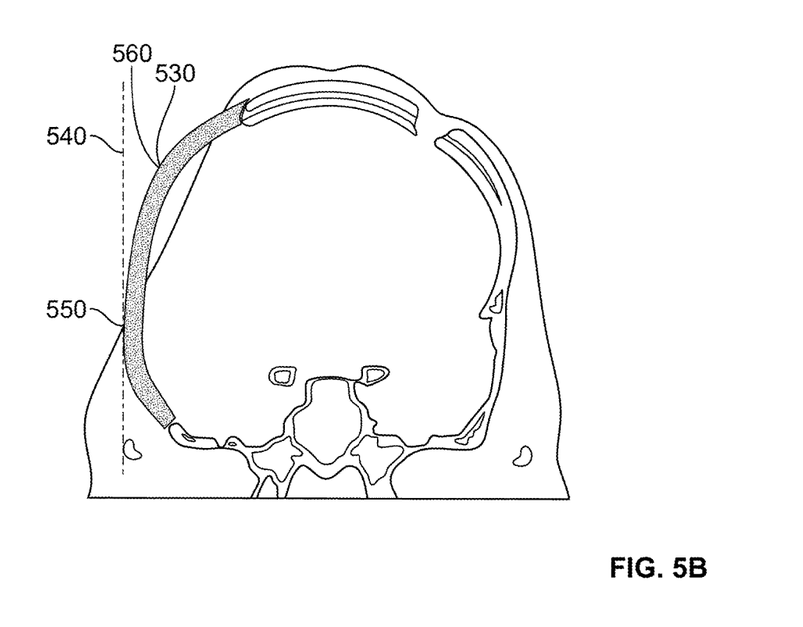
FIG. 5B is a coronal cross-section of the 3D reconstruction of FIG. 5A taken along line 5B thereof showing the location of the most lateral portion of the augmented portion of the patient-specific cranial implant.

In determining the location of the most lateral portion of the outer surface of augment portion 500, the preliminary implant model 400 is extended laterally away from sagittal plane 410, for example, until the outer surface of augment portion 500 meets the most lateral portion of the zygomatic arch 550 of the patient as shown in FIG. 5B. The most lateral portion of the zygomatic arch is depicted by vertical line 540 in the coronal cross section shown in FIG. 5B. In the coronal plane, the temporal region of the preliminary implant model is augmented by drawing a substantially straight or slightly curved line 560 from the temporal crest 530 until line 560 intersects vertical line 540 adjacent the most lateral portion of the zygomatic arch 550. Temporal crest 530 is located at the point where there is a change in tangency of the pterional skull as pertinent in the present scenario. Of note, various other areas of the temporal (i.e. pterional) skeleton could be assessed for dual-purpose reconstruction. This process is preferably repeated in several different two dimensional ("2D") coronal cross-sections. The updated implant models created in the 2D cross-sections are then combined using the CT segmentation software in order to create the 3D updated implant model shown in FIGS. 6A-6B, for example.

Figure 6A:
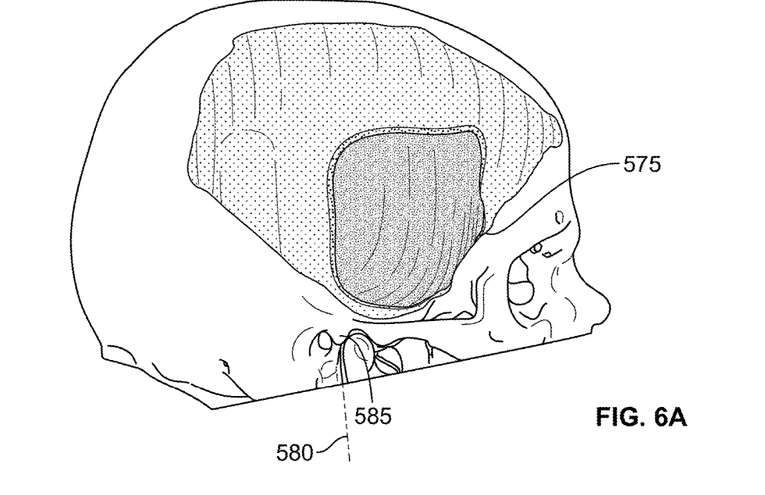
FIG. 6A is a lateral view of the 3D reconstruction of the patient-specific cranial implant.
Figure 6B:
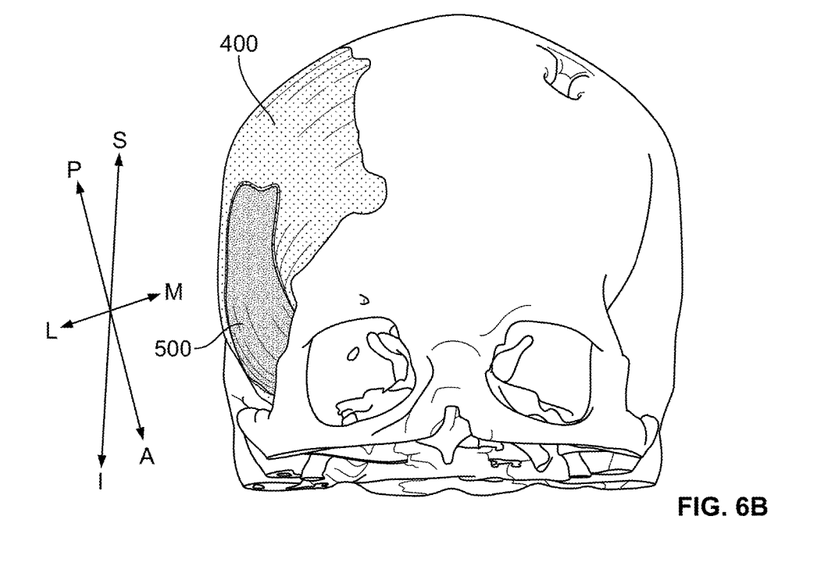
FIG. 6B is a frontal view of the 3D reconstruction of the patient-specific cranial implant shown in FIG. 6A.

As shown in FIGS. 6A-6B, augment portion 500 extends posteriorly from the lateral orbital rim 575 to a vertical line 580 perpendicular to the sagittal plane drawn through the external acoustic meatus 585. Augment portion 500 should extend as far posteriorly as it does superiorly so that the augmented area is roughly square as shown in FIG. 5A. The augmented area is roughly outlined by box 570 overlying updated implant model 600 in FIG. 5A.

Figure 7A:
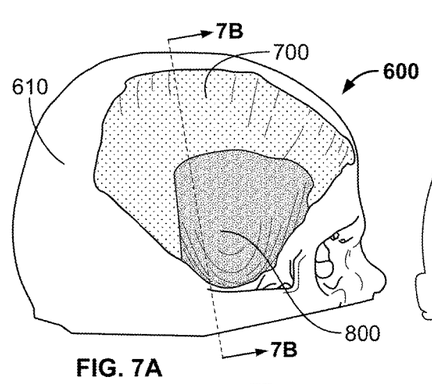
FIG. 7A is a lateral view of a 3D reconstruction of another embodiment of a patient-specific cranial implant having a base portion and at least one augmented portion.
Figure 7B:
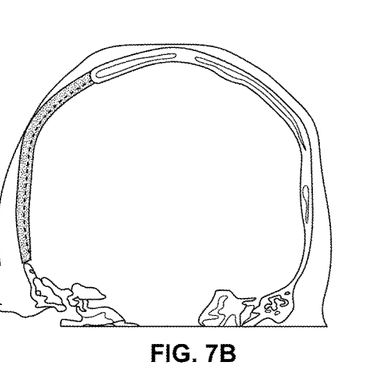
FIG. 7B is a coronal cross-section of the 3D reconstruction of FIG. 7A taken along line 7B thereof, the cross-section showing the configuration of the base portion and the augmented portion at a posterior location of the pterional region of the skull.
Figure 7C:
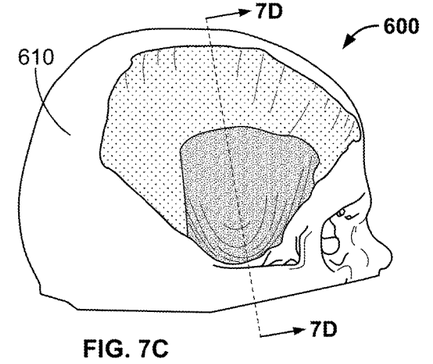
FIG. 7C is another lateral view of a 3D reconstruction of the patient-specific cranial implant of FIG. 7A.
Figure 7D:
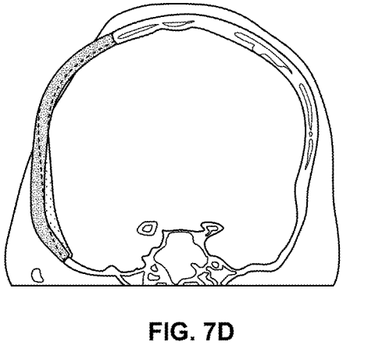
FIG. 7D is a coronal cross-section of the 3D reconstruction of FIG. 7C taken along line 7D thereof, the cross-section showing the configuration of the base portion and the augment portion at a central location of the pterional region of the skull.
Figure 7E:
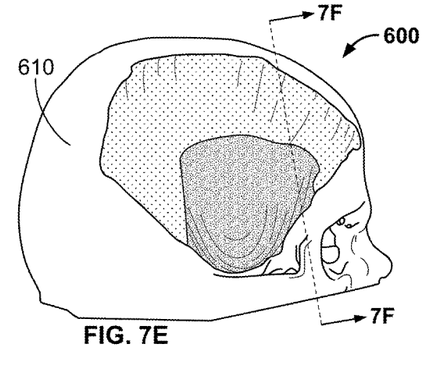
FIG. 7E is yet another lateral view of a 3D reconstruction of the patient-specific cranial implant of FIG. 7A.
Figure 7F:
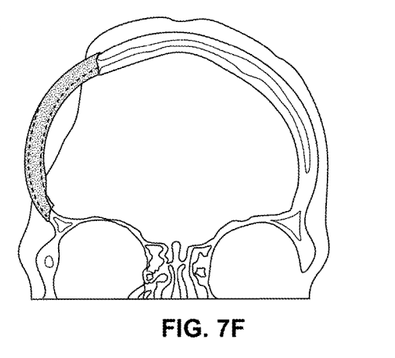
FIG. 7F is a coronal cross-section of the 3D reconstruction of FIG. 7E taken along line 7F thereof, the cross-section showing the configuration of the base portion and the augmented portion at an anterior location of the pterional region of the skull.

FIGS. 7A, 7C, and 7E are a series of lateral views of a 3D reconstruction of one embodiment of an updated implant model 600 implanted in a model of a bone void of a patient's skull 610, each of these views including a section line 7B, 7D, and 7F, respectively. Section lines 7B, 7D, and 7F are each situated at different locations on the 3D models. Section line 7B is located in a posterior region, section line 7D is located in a central region, and section line 7F is located in an anterior aspect of the pterional region of the patient's skull 610 in these lateral views. FIGS. 7B, 7D and 7F are coronal cross-sectional views that correspond to FIGS. 7A, 7C and 7E, respectively. Each of these coronal cross-sectional views show updated implant model 600 including a preliminary implant model 700 and an augment portion 800. As can be seen most clearly in FIG. 7D, augment portion 800 is not symmetric to contralateral bone as is preliminary implant model 700. Most of the bulk reproduction of augment portion 800 is created in this central region of the pterion.

Figures 8A, 8C:
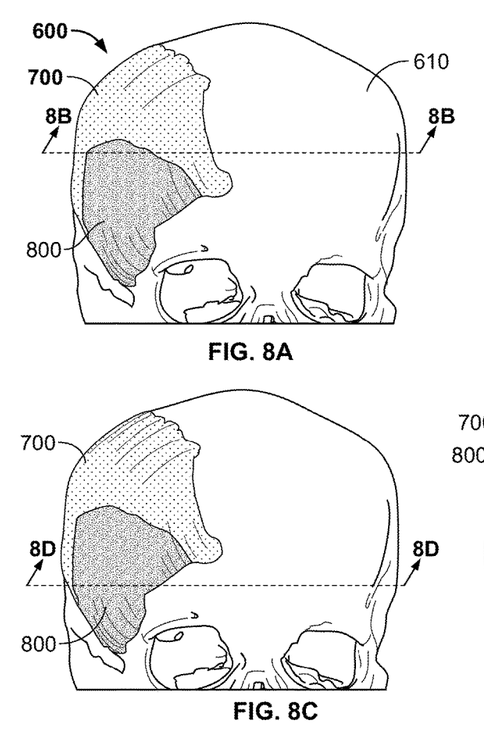
FIG. 8A is a frontal view of a 3D reconstruction of the patient-specific cranial implant shown in FIG. 7A.
FIG. 8C is another frontal view of a 3D reconstruction of the patient-specific cranial implant of FIG. 7A.
Figures 8B, 8C, 8D:
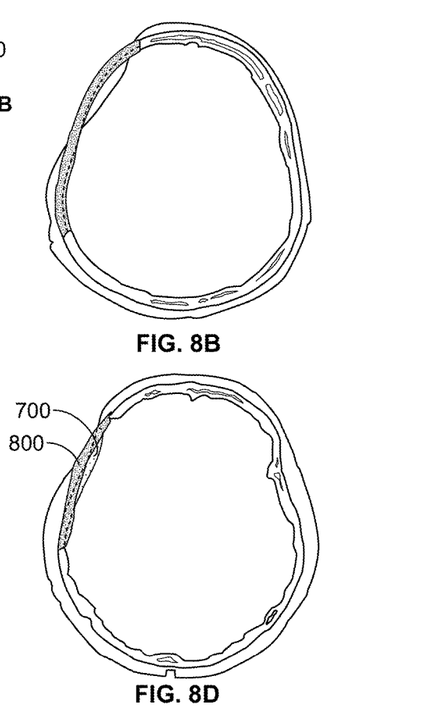
FIG. 8B is an axial cross-section of the 3D reconstruction of FIG. 8A taken along line 8B thereof, the cross-section showing the configuration of the base portion and the augmented portion at a superior location of the pterional region of the skull.
FIG. 8D is an axial cross-section of the 3D reconstruction of FIG. 8C taken along line 8D thereof, the cross-section showing the configuration of the base portion and the augmented portion at a central location of the pterional region of the skull.
Figure 8E:
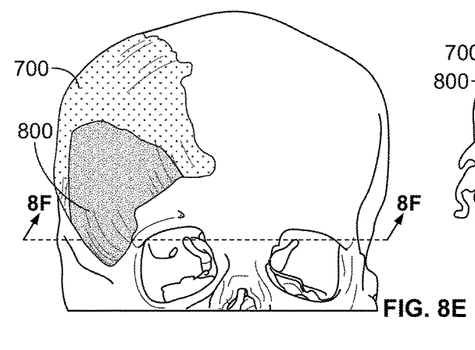
FIG. 8E is yet another frontal view of a 3D reconstruction of the patient-specific cranial implant of FIG. 7A.
Figure 8F:
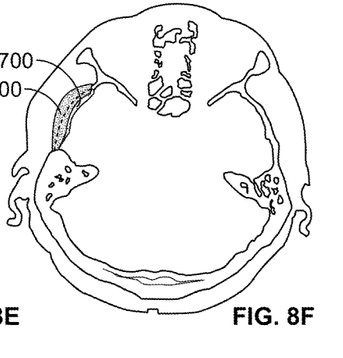
FIG. 8F is an axial cross-section of the 3D reconstruction of FIG. 8E taken along line 8F thereof, the cross-section showing the configuration of the base portion and the augmented portion at an inferior location of the pterional region of the skull.

FIGS. 8A, 8C, and 8E are a series of frontal views of updated implant model 600 each having a section line 8B, 8D, and 8F, respectively. Section lines 8B, 8D, and 8F are each situated at different locations on the 3D models. Section line 8B is located in a superior region, section line 7D is located in a central region, and section line 8F is located in an inferior aspect of the pterional region of the patient's skull in these lateral views. FIGS. 8B, 8D and 8F are axial cross-sectional views that correspond to FIGS. 8A, 8C and 8E, respectively. Each of these axial cross-sectional views shows the difference between preliminary implant model 700 and an updated implant model including augment portion 800. As can be seen most clearly in FIG. 8D, augment portion 800 is not symmetric to contralateral bone as is preliminary implant model 700. It is designed and modified specifically to make up for the soft tissue discrepancy. In other words, it can be used for deformity prophylaxis and/or secondary correction.

Each patient-specific cranial implant of the present invention will be customized to fit the unique bony void and individual anthropometry of the patient, and therefore, the design inputs described above may be adjusted as needed. For example, with respect to bilateral deficits, the dual-purpose implants can be fabricated used gender-specific anthropometric norms. Once the design of updated implant model 600 is finalized using the CAD software, a patient-specific craniofacial implant may be manufactured using any one of many known manufacturing techniques, such as steriolithography, milling, and molding, for example. The implant can then be manufactured, for example, from alloplastic materials such as PMMA, MEDPOR®, and PEEK.

Although the invention herein has been described with reference to particular embodiments, it is to be understood that these embodiments are merely illustrative of the principles and applications of the present invention. It is, therefore, to be understood that numerous modifications may be made to the illustrative embodiments and that other arrangements may be devised without departing from the spirit and scope of the present invention as defined by the appended claims.

The invention claimed is:

1. A craniofacial implant for filling a void in a pterional region of a skull of a patient and for replacing soft tissue comprising:
    a base portion defining a perimeter of the craniofacial implant, the base portion having an upper surface curved in a medial to lateral direction, a superior to inferior direction, and a posterior to anterior direction, the base portion having a first volume; and
    a curved augment portion preoperatively designed and positioned relative to the base portion, based upon specific anthropometry of the patient, accounting for soft tissue loss overlying at least a portion of the void in the pterional region of the skull of the patient, the curved augment portion protruding outwardly from the upper surface of the base portion and having a second volume,
    wherein the craniofacial implant has a total volume including the first and second volumes and wherein an outer surface of the craniofacial implant is asymmetrical to contralateral bone of the skull of the patient.

2. The craniofacial implant of claim 1, wherein the curved augment portion has an upper surface curved in the medial to lateral direction, the superior to inferior direction, and the posterior to anterior direction.

3. The craniofacial implant of claim 2, wherein the upper surfaces of the base portion and the curved augment portion each have a first radius of curvature in the medial to lateral direction, and wherein the first radius of curvature of the base portion is larger than the first radius of curvature of the curved augment portion.

4. The craniofacial implant of claim 3, wherein the upper surfaces of the base portion and the curved augment portion each have a second radius of curvature in the superior to inferior direction, and wherein the second radius of curvature of the base portion is larger than the second radius of curvature of the curved augment portion.

5. The craniofacial implant of claim 4, wherein the upper surfaces of the base portion and the curved augment portion each have a third radius of curvature in the posterior to anterior direction, and wherein the third radius of curvature of the base portion is larger than the third radius of curvature of the curved augment portion.

6. The craniofacial implant of claim 2, wherein the upper surfaces of the base portion and the curved augment portion are convex.

7. The craniofacial implant of claim 6, wherein the base portion and the curved augment portion each have concave inner surfaces.

8. A craniofacial implant for filling a void in a pterional region of a skull of a patient and for replacing soft tissue comprising:
    a base portion defining a perimeter of the craniofacial implant, the base portion having an upper surface curved in a medial to lateral direction, a superior to inferior direction, and a posterior to anterior direction, the base portion having a first volume that accounts for the void in the skull of the patient; and
    a curved augment portion preoperatively designed and positioned relative to the base portion, based upon specific anthropometry of the patient, accounting for soft tissue loss overlying at least a portion of the void in the pterional region of the skull of the patient, the curved augment portion protruding outwardly from the upper surface of the base portion and having a second volume,
    wherein the craniofacial implant has a total volume including the first and second volumes, and wherein an outer surface of the craniofacial implant is asymmetrical to contralateral bone of the skull of the patient.

9. The craniofacial implant of claim 8, wherein the curved augment portion has an upper surface curved in the medial to lateral direction, the superior to inferior direction, and the posterior to anterior direction.

10. The craniofacial implant of claim 9, wherein the upper surfaces of the base portion and the curved augment portion each have a first radius of curvature in the medial to lateral direction, and wherein the first radius of curvature of the base portion is larger than the first radius of curvature of the curved augment portion.

11. The craniofacial implant of claim 10, wherein the upper surfaces of the base portion and the curved augment portion each have a second radius of curvature in the superior to inferior direction, and wherein the second radius of curvature of the base portion is larger than the second radius of curvature of the curved augment portion.

12. The craniofacial implant of claim 11, wherein the upper surfaces of the base portion and the curved augment portion each have a third radius of curvature in the posterior to anterior direction, and wherein the third radius of curvature of the base portion is larger than the third radius of curvature of the curved augment portion.

13. The craniofacial implant of claim 9, wherein the upper surfaces of the base portion and curved augment portion are convex.

14. The craniofacial implant of claim 13, wherein the base portion and the curved augment portion each have concave inner surfaces.

15. A craniofacial implant for filling a void in a pterional region of a skull of a patient and for replacing soft tissue comprising:
- a base portion defining a perimeter of the craniofacial implant, the base portion having an upper surface curved in a medial to lateral direction, a superior to inferior direction, and a posterior to anterior direction, the upper surface of the base portion having a first radius of curvature in the medial to lateral direction; and
- an augment portion preoperatively designed and positioned relative to the base portion, based upon specific anthropometry of the patient, accounting for soft tissue loss overlying at least a portion of the void in the pterional region of the skull of the patient, the curved augment portion protruding outwardly from the upper surface of the base portion and having an upper surface curved in a medial to lateral direction, a superior to inferior direction, and a posterior to anterior direction, the upper surface of the augment portion having a second radius of curvature in the medial to lateral direction,
- wherein the first radius of curvature of the base portion is larger than the second radius of curvature of the augment portion such that an outer surface of the craniofacial implant is asymmetrical to contralateral bone of the skull of the patient.

16. The craniofacial implant of claim 15, wherein the base portion has a first volume that accounts for the void in the skull of the patient and the augment portion has a second volume that accounts for soft tissue loss overlying at least a portion of the void in the pterional region of the skull of the patient, and wherein the craniofacial implant has a total volume including the first and second volumes.

* * * * *